(12) United States Patent
Kanda et al.

(10) Patent No.: US 8,865,418 B2
(45) Date of Patent: Oct. 21, 2014

(54) IMMUNOANALYTICAL METHOD AND SYSTEM USING MASS SPECTROMETRY TECHNOLOGY

(75) Inventors: Katsuhiro Kanda, Hitachinaka (JP); Makoto Nogami, Tsuchiura (JP); Izumi Waki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 595 days.

(21) Appl. No.: 13/146,952

(22) PCT Filed: Feb. 9, 2010

(86) PCT No.: PCT/JP2010/051904
§ 371 (c)(1),
(2), (4) Date: Aug. 4, 2011

(87) PCT Pub. No.: WO2010/092958
PCT Pub. Date: Aug. 19, 2010

(65) Prior Publication Data
US 2011/0287446 A1    Nov. 24, 2011

(30) Foreign Application Priority Data
Feb. 10, 2009    (JP) .................................. 2009-029111

(51) Int. Cl.
*G01N 33/53*    (2006.01)
*G01N 31/00*    (2006.01)
*G01N 33/68*    (2006.01)

(52) U.S. Cl.
CPC .................................. *G01N 33/6848* (2013.01)
USPC ........... 435/7.21; 435/7.1; 436/501; 436/518; 424/9.1; 424/520; 422/430; 530/300; 530/350

(58) Field of Classification Search
None
See application file for complete search history.

(56) References Cited

U.S. PATENT DOCUMENTS

| | | | |
|---|---|---|---|
| 2004/0224359 A1 | 11/2004 | Madonna et al. | |
| 2005/0239211 A1 | 10/2005 | Uchihara et al. | |
| 2006/0051741 A1 | 3/2006 | Tanaka et al. | |
| 2009/0023159 A1 | 1/2009 | Mendez | |

FOREIGN PATENT DOCUMENTS

| | | |
|---|---|---|
| JP | 11-201953 A | 7/1999 |
| JP | 2005-98830 A | 4/2005 |
| JP | 2005-524394 A | 8/2005 |
| JP | 2005-291823 A | 10/2005 |
| JP | 2006-126013 A | 5/2006 |
| JP | 2008-532984 A | 8/2008 |
| WO | 2004/031759 A1 | 4/2004 |

*Primary Examiner* — Lisa Cook
(74) *Attorney, Agent, or Firm* — Mattingly & Malur, PC

(57) ABSTRACT

An immunoanalytical system in which, after a sample such as a patient's serum is subjected to a pretreatment by an immunological pretreatment device, the sample is subjected to light detection by an immunological photometric detection system. Subsequently, the mass spectrometric pretreatment device performs a pretreatment, and the mass spectrometric detection system performs mass spectrometry. The mass spectrometric detection system performs mass spectrometry on components contained in a supernatant. A signal intensity and peak area for each of components are calculated from an obtained chromatograph. A quantitative value measured based on the immunoanalytical method is calculated for each of the components on the basis of the relative ratios of the components.

5 Claims, 18 Drawing Sheets

201: MAGNETIC PARTICLE
202: AVIDIN
203: BIOTIN
204: PRIMARY ANTIBODY
205: COMPONENT TO BE MEASURED
206: SECONDARY ANTIBODY
207: ENZYME
208: SUBSTRATE
209: CHEMILUMINESCENCE
210: MAGNETIC BODY
211: DETECTOR

FIG.3

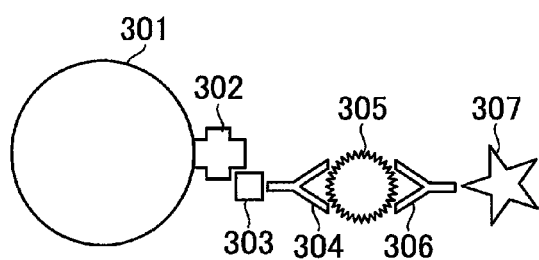

301: MAGNETIC PARTICLE
302: AVIDIN
303: BIOTIN
304: PRIMARY ANTIBODY
305: COMPONENT TO BE MEASURED
306: SECONDARY ANTIBODY
307: ENZYME

▽

ANTIGEN (COMPONENT TO BE MEASURED) IS LIBERATED BY ACID TREATMENT, ALKALINE TREATMENT AND IONIC STRENGTH TREATMENT

▽

MAGNETIC BEADS ARE COLLECTED BY MAGNETIC FORCE AND SUPERNATANT IS COLLECTED

▽

ANTIGEN (COMPONENT TO BE MEASURED) IS EXTRACTED WHEN NECESSARY

▽

BUFFER SUBSTITUTION WHEN NECESSARY

▽

SAMPLE IS SUPPLIED TO MASS SPECTROMETRIC DETECTION SYSTEM

FIG.4

| COMPONENT | | CROSS-REACTIVITY (%) | PHARMACOLOGICAL ACTIVITY (IC50, ng/ml) |
|---|---|---|---|
| TACROLIMUS | | 100.0 | 0.11 |
| METABOLITES | M-I | 0.0 | 1.71 |
| | M-II | 109.0 | 0.11 |
| | M-III | 90.5 | >1,000 |
| | M-IV | 8.8 | 3.13 |
| | M-V | 92.2 | >1,000 |
| | M-VI | 0.0 | 8.78 |
| | M-VII | 0.0 | >1,000 |
| | M-VIII | 0.0 | 15.27 |

FIG.5

| COMPONENT | | ASSUMED RELATIVE VALUE (%) OF SIGNAL (OR PEAK AREA) IN MS MEASUREMENT | PROPORTION (%) | CORRECTED MEASURED VALUE (ng/ml) |
|---|---|---|---|---|
| TACROLIMUS | | 100 | 76.9 | 7.7 |
| METABOLITES | M-II | 20 | 15.4 | 1.5 |
| | M-IV | 10 | 7.7 | 0.8 |
| TOTAL | | — | 100.0 | 10.0 |

601: MAGNETIC PARTICLE
602: AVIDIN
603: BIOTIN
604: PRIMARY ANTIBODY
605: COMPONENT TO BE MEASURED
606: MAGNETIC BODY

FIG.12

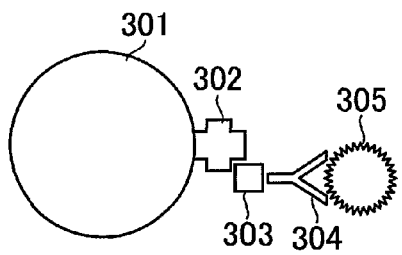

301: MAGNETIC PARTICLE
302: AVIDIN
303: BIOTIN
304: PRIMARY ANTIBODY
305: COMPONENT TO BE MEASURED

▽

ANTIGEN (COMPONENT TO BE MEASURED) IS LIBERATED BY ACID TREATMENT, ALKALINE TREATMENT AND IONIC STRENGTH TREATMENT

▽

MAGNETIC BEADS ARE COLLECTED BY MAGNETIC FORCE AND SUPERNATANT IS COLLECTED

▽

ANTIGEN (COMPONENT TO BE MEASURED) IS EXTRACTED WHEN NECESSARY

▽

BUFFER SUBSTITUTION WHEN NECESSARY

▽

SAMPLE IS SUPPLIED TO MASS SPECTROMETRIC DETECTION SYSTEM

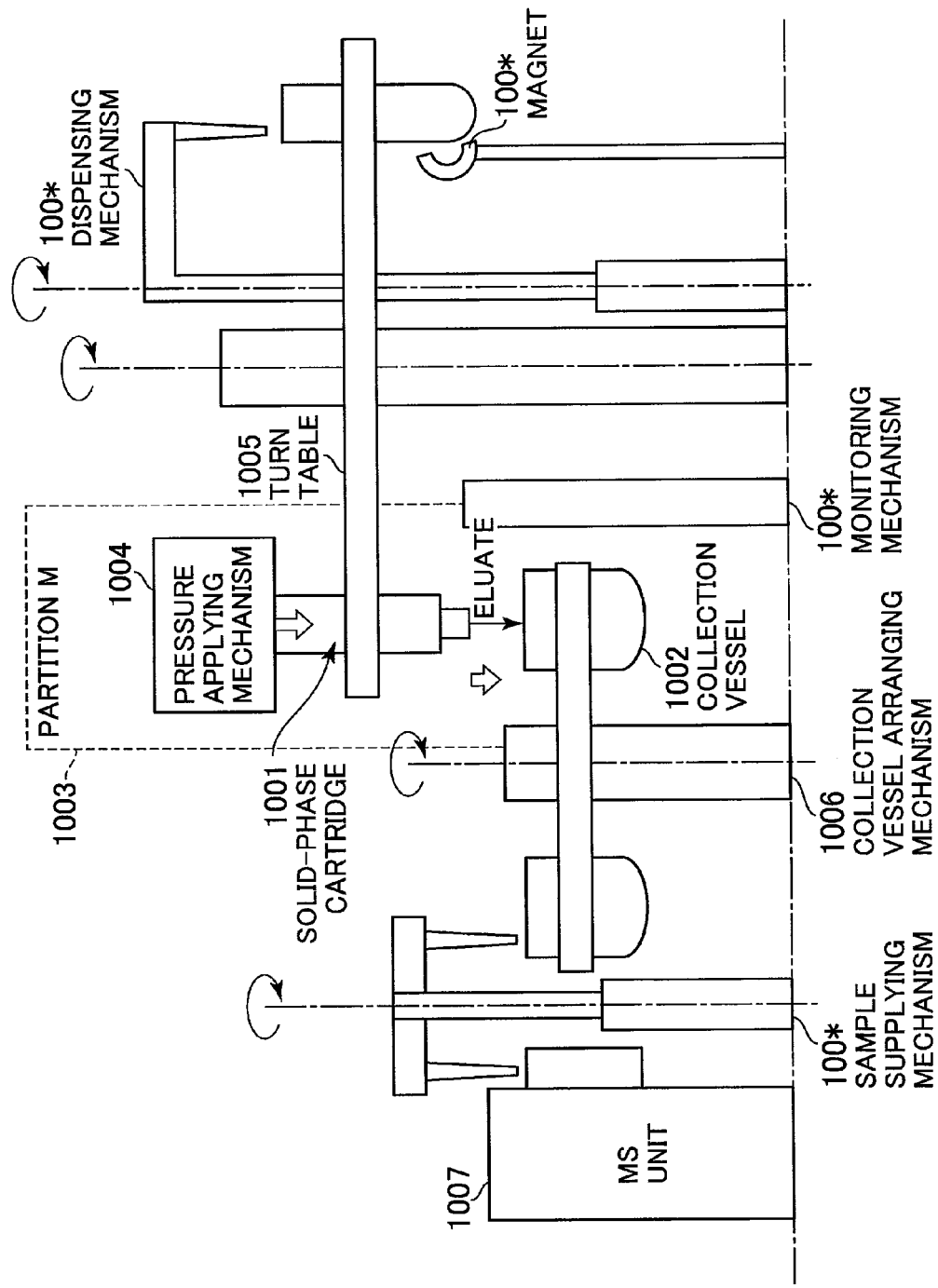

FIG.18

| | STEP | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| SAMPLE 1 | IMMUNOLOGICAL REACTION | S | T | U | V | W | X | Y | Z→ | | | | | | | | | | | | |
| SAMPLE 1 | SOLID-PHASE EXTRACTION | | | A | B | C | D | E | ↓F | G | H | I | J | K | L | M | N | | | | |
| SAMPLE 2 | IMMUNOLOGICAL REACTION | | S | T | U | V | W | X | Y | Z→ | | | | | | | | | | | |
| SAMPLE 2 | SOLID-PHASE EXTRACTION | | | | A | B | C | D | E | ↓F | G | H | I | J | K | L | M | N | | | |
| SAMPLE 3 | IMMUNOLOGICAL REACTION | | | S | T | U | V | W | X | Y | Z→ | | | | | | | | | | |
| SAMPLE 3 | SOLID-PHASE EXTRACTION | | | | | A | B | C | D | E | ↓F | G | H | I | J | K | L | M | N | | |
| SAMPLE 4 | IMMUNOLOGICAL REACTION | | | | S | T | U | V | W | X | Y | Z→ | | | | | | | | | |
| SAMPLE 4 | SOLID-PHASE EXTRACTION | | | | | | A | B | C | D | E | ↓F | G | H | I | J | K | L | M | N | |

ADD ANTIGEN EXTRACTION SOLUTION TO SOLID-PHASE EXTRACTION AGENT

IMMUNOANALYTICAL METHOD AND SYSTEM USING MASS SPECTROMETRY TECHNOLOGY

TECHNICAL FIELD

The present invention relates to an immunoanalytical method and an immunoanalytical system which are used for clinical inspection.

BACKGROUND ART

One of inspection methods that are widely used for clinical inspection is an immunological method. In the immunological method, an antibody that specifically recognizes a component to be measured is used. For example, after the antibody (primary antibody) captures a component that is to be measured and is contained in a specimen, the component is detected using a secondary antibody that selectively captures the primary antibody. The secondary antibody is provided with a label for higher detection sensitivity. The label is, for example, a fluorescent material, a material that is necessary for enzyme chemiluminescence or the like. Since the immunological method is a measurement technique that can simply detect a component with high sensitivity, the immunological method is suitable for a quantitative measurement of minute amounts of components contained in a specimen.

However, the immunological method involves a problem of cross-reactivity. The cross-reactivity is an effect that causes the primary antibody to capture not only a component to be measured that is necessary to recognize but also a molecule (such as a metabolite of the component to be measured) with a structure similar to that of the component to be measured. This means that a quantitative result is higher than the true value and the component to be measured cannot be accurately quantified.

In particular, small molecule compounds, having low-molecular weight, tend to exhibit stronger cross-reactivity. To develop an antibody for these target molecules, it is necessary to increase the molecular size of the component by adding a carrier protein to the component to be measured; a part other than a part to which the carrier protein is added can be an epitope. Therefore, it is often difficult to identify the structural difference between a metabolite and the target component depending on the part to which the carrier protein is added. In order to suppress the cross-reactivity, it is necessary to create a primary antibody that is capable of identifying the difference between molecules with similar structures. However, it is difficult to create such a primary antibody and a lot of effort with cost and labor is required for the creation of the primary antibody, which is not efficient.

In contrast to the immunological method, a mass spectrometry method detects a component on the basis of the mass of the component to be measured. Thus, the mass spectrometry method is a measurement technique capable of identifying the difference between the component to be measured and another molecule (such as a metabolite) with a structure similar to that of the component. Especially, a method for MS/MS analysis and a method for MS(n) analysis are techniques capable of identifying the difference between components with similar structures with high accuracy by fragmenting the components to be measured into fragment ions. In addition, since the mass spectrometry method does not require a special reagent such as an antibody, it is possible to reduce the cost and effort.

There are known examples in which another analysis method or process is combined with the mass spectrometry analysis, where the analysis method or process is performed before execution of the mass spectrometry analysis. For example, western blotting (refer to Patent Document 1), collection of target bacteria using magnetic beads (refer to Patent Document 2), pull-down assay (refer to Patent Document 3), collection of target substances onto an organic thin film (Patent Document 4), or gel electrophoresis (Patent Document 5) is performed before the mass spectrometry starts.

PRIOR ART DOCUMENTS

Patent Document 1: JP-2006-126013-A
Patent Document 2: JP-2005-524394-A
Patent Document 3: JP-2005-098830-A
Patent Document 4: JP-2005-291823-A
Patent Document 5: WO 2004-031759

SUMMARY OF THE INVENTION

Problems to be Solved by the Invention

Although the mass spectrometry method has an excellent feature of identifying and detecting a component, it is necessary to prepare an internal standard substance or the like when the component is to be quantified.

In addition, the mass spectrometry involves ionization of the component and accuracy of the quantification is determined by the efficiency of ionization. Thus, it is necessary to carefully select the internal standard substance.

The most preferable internal standard is a molecule which is produced by labeling the analyte component by stable-isotopes, which are so-called stable-isotope-labeled internal standards. In this case, however, it may be costly to synthesize such stable-isotope-labeled components, or it can be problematic if synthesis of isotope-labeled components is difficult for some components.

If a device and a method are provided which eliminate the aforementioned cross-reactivity in the immunological method and solve the problem with quantification of components in the mass spectrometry method, an innovative high-accuracy clinical inspection technique can be realized.

An object of the present invention is to provide an immunoanalytical method and an immunoanalytical system that allow for elimination of cross-reactivity in the immunological method and solve the problem with quantification of components in the mass spectrometry method.

Means for Solving the Problems

In order to accomplish the object, the present invention is configured as follows.

An immunoanalytical method and an immunoanalytical system include capturing an object to be measured, the object being contained in a sample solution, by using an antibody during a pretreatment process based on the immunoanalytical method; collecting components to be measured from the captured object to be measured; and performing mass spectrometry on the collected components to be measured in conformity with a mass spectrometry method and analyzing the components of the object to be measured.

Preferably, an immunoanalytical method and an immunoanalytical system include capturing an object to be measured, the object being contained in a sample solution, by using an antibody during a pretreatment process based on the immunoanalytical method; quantifying the captured object to be measured; collecting the object to be measured from a waste liquid resulting after the captured object to be measured has been subjected to the quantification; and performing mass spectrometry on the collected object to be measured in conformity with a mass spectrometry method and measuring components of the object measured based on the immunoanalytical method.

Effect of the Invention

An immunoanalytical method and an immunoanalytical system can be achieved which allow for elimination of cross-reactivity in the immunological method and solve the problem with quantification of components in the mass spectrometry method.

BRIEF DESCRIPTION OF THE DRAWINGS

FIG. 3 is a diagram showing a waste liquid process in the immunological method.

FIG. 4 is a diagram showing cross-reactivity of tacrolimus and a medicinal effect of the tacrolimus.

FIG. 5 is a diagram showing data on an object that is to be measured and is contained in a patient's specimen.

FIG. 12 is a diagram showing a collection of a component to be measured from a product of the pretreatment for the immunological method.

FIG. 17 is a side view of the configuration of the system that is related to the solid-phase extraction process.

FIG. 18 is a diagram showing a sequence of the immunological reaction process and the solid-phase extraction process.

MODE FOR CARRYING OUT THE INVENTION

Embodiments of the present invention are described below with reference to the accompanying drawings.

First Embodiment

The first embodiment of the present invention describes an example of a detection of a component in mass spectrometry from a waste liquid obtained after light detection in an immunological method.

Figure 1:
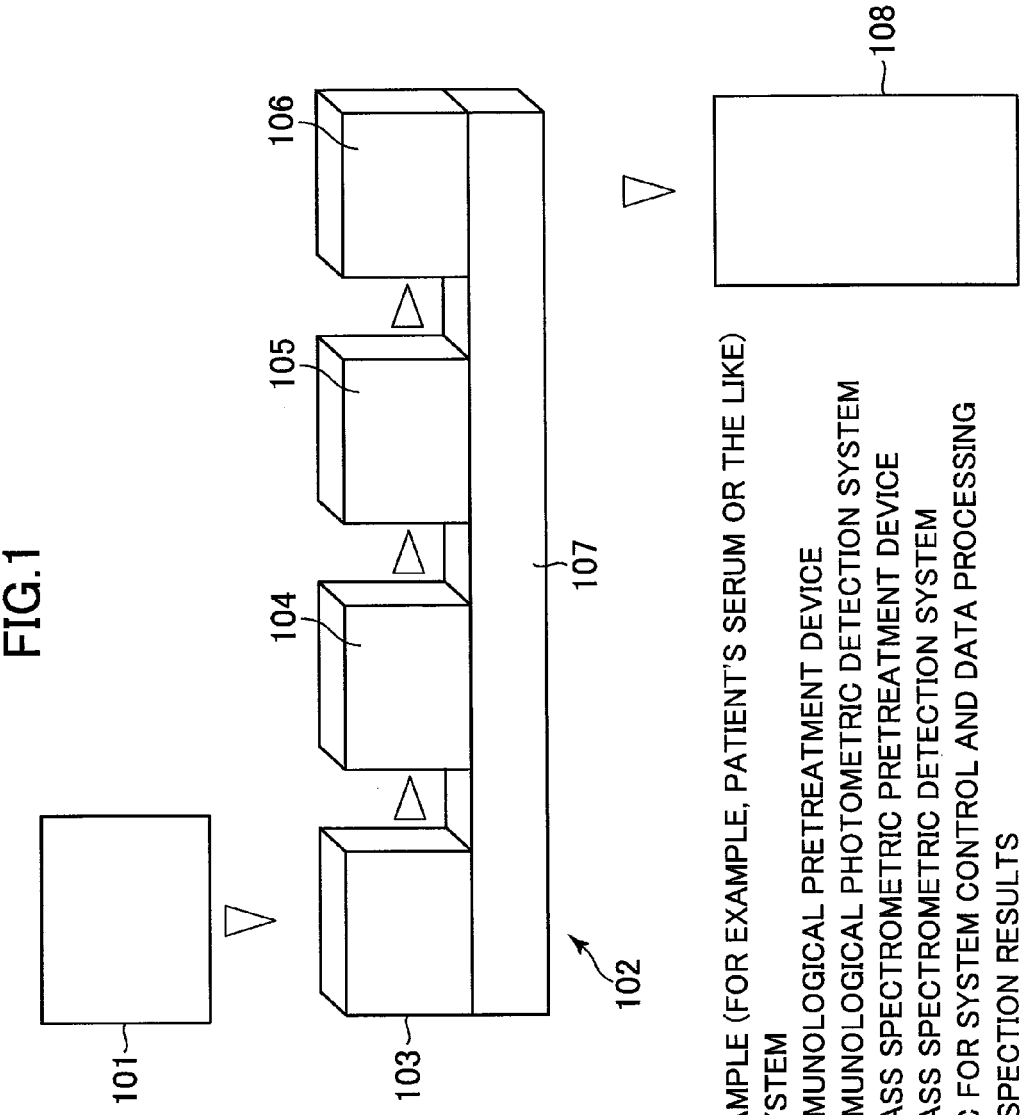
FIG. 1 is a diagram showing an outline configuration of an entire system for immunoanalysis of samples according to a first embodiment of the present invention and showing the flow of a measurement.

FIG. 1 is a diagram showing an outline configuration of an entire immunoanalytical system 102 according to the first embodiment and showing the flow of a measurement.

A sample 101 such as a patient's serum is subjected to a pretreatment by an immunological pretreatment device 103. After the pretreatment, the sample 101 is subjected to light detection by an immunological photometric detection system 104. Then, a pretreatment is performed on the sample by a mass spectrometric pretreatment device 105, and mass spectrometry is performed on the sample by a mass spectrometric detection system 106. The sample immunoanalytical system 102, the immunological pretreatment device 103, the immunological photometric detection system 104, the mass spectrometric pretreatment device 105, and the mass spectrometric detection system 106 are controlled in operation by a personal computer 107 for system control and data processing. The assay results 108 are displayed on a display of the personal computer 107.

Figure 2:
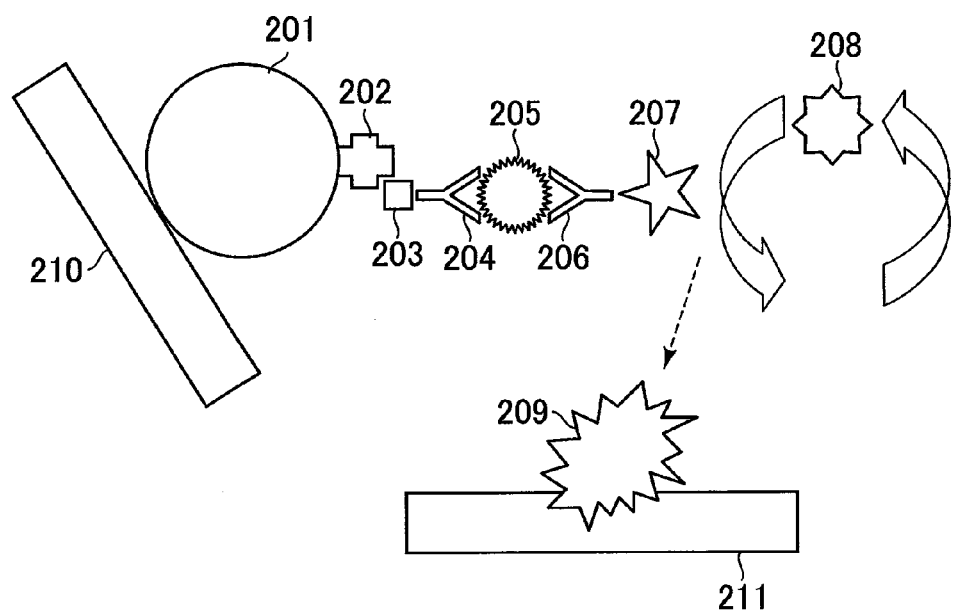
FIG. 2 is a diagram showing an immunological method.

Specifically, the immunological pretreatment device 103 subjects to pretreatment a component that is to be measured and is contained in the sample (for example, whole blood, blood plasma, a serum, urine or the like) derived from a biological body, according to an automatic immunoanalytical method. The immunological photometric detection system 104 then allows an antibody that specifically recognizes the component to selectively capture the pretreated component to be measured. The antibody is bound with a magnetic particle by avidin-biotin binding or the like in advance. As shown in FIG. 2, after a magnetic particle 201 captures a target analyte component 205 (to be measured) through antibodies 202, 203, 204 and 206, the magnetic particle is collected by a magnetic force of a magnetic body 210. Then, an unnecessary element or the like in the ambient solution around the magnetic particle 201 is washed away. After that, the magnetic particle 201 is subjected to sandwich assay using a labeled anti-immunoglobulin antibody such that a detector 211 detects and quantifies the component to be measured.

This quantitative measurement value includes not only a value of the component to be measured but also a value of another substance (such as a metabolite derived from the component) that has a structure similar to that of the component and thereby causes cross-reactivity. Therefore, the thus-obtained quantitative value tends to be higher than the true quantitative value of the component that one desires to measure.

To avoid this, a sample captured by the immunological method or a waste liquid obtained after the measurement using the immunological method is reused. When the proportion (relative ratio) of a component such as a substance contained in such a sample or waste liquid and causing cross-reactivity is calculated by the mass spectrometry method, the quantitative value of the captured component is individually calculated in a value close to the true value based on the quantitative value calculated by the immunological method.

The mass spectrometric pretreatment device 105 collects the component to be measured from the sample (waste liquid) used in the immunological method. For example, the waste liquid obtained after the immunological measurement is subjected to an acid treatment, an alkaline treatment, an ionic strength treatment and the like so that an antigen-antibody bond is dissociated, and the antigen (component to be measured) is liberated from the antibody. As shown in FIG. 3, magnetic beads are collected under a magnetic force of a magnetic particle 301 again, and a supernatant is collected. After subjected to a solvent substitution, the supernatant is supplied to the mass spectrometric detection system 106.

Depending on properties of the component to be measured, a component that is contained in the supernatant may be separated from the supernatant by a chromatographic method such as size fractionation or fractionated by enzyme digestion when necessary.

The mass spectrometric detection system 106 performs mass-analysis of components contained in the supernatant. Signal intensity and a peak area are calculated for each of the components on the basis of the chromatograph obtained. Using the relative intensity ratios of the components, it is possible to calculate the proportion of the quantitative value for each of the components using the total quantitative value obtained by the immunological method and their relative ratios obtained by mass spectrometry. The quantitative value is corrected for each of the components by multiplying the quantitative value calculated from the immunological method by the aforementioned relative ratio of the component.

Thus, although the quantitative value of the component (to be measured) obtained by the immunological method is affected by the cross-reactivity or the like under the application of the immunological method, the above scheme allows such a quantitative value to be re-calculated as a value close to the true value. In addition, the proportions of substances that have similar structures and may cause the cross-reactivity can be quantitatively calculated thereby.

Representative examples of the substances with similar structures include metabolites of the component to be measured. For example, when the component to be measured is a medical remedy, it is important for management of the administration of medication to know the medical remedy to be measured and the proportion (profile) and quantitative value of a metabolite of the medical remedy. Although a conventional immunological method cannot calculate the concentration of the metabolite, such calculation is enabled according to the present invention.

For example, when the component to be measured is tacrolimus, which is an immunosuppressant drug, the following are known as metabolites: M-I (13-o-demethyl); M-II (31-o-demethyl); M-III (15-o-demethyl); M-IV (12-o-hydroxyl); M-V (15, 31-o-didemethyl); M-VI (13, 31-o-didemethyl); M-VII; and M-VIII as shown in FIG. 4 (K. Iwasaki, Drug Metab, Pharmacokinet., 22(5), 328-335, 2007). Cross-reactivity caused by the metabolites in enzyme immunoassay with a monoclonal antibody used for evaluation is 0%, 109%, 90.5%, 8.8%, 92.2%, 0%, 0% and 0%, respectively for each metabolite. For example, when the tacrolimus is administered to a patient subjected to an organ transplant, and the concentration of the tacrolimus in blood is measured by the immunological method using the antibody, the measured quantitative value may include not only the tacrolimus but also the metabolites M-II, M-IV and M-V.

Among the eight types of the metabolites M-I to M-VIII, the effects of immune suppression are exhibited by the metabolites M-I, M-II, M-IV, M-VI and M-VIII. If the aforementioned cross-reactivity is taken into account, it is recognized that the metabolites M-II and M-IV each have both properties of the cross-reactivity and the immune suppression effect. When the concentration of the tacrolimus in blood is measured by the immunological method using the monoclonal antibody used by Iwasaki for the test, it is essential for management of the administration of medication to know the concentrations of the metabolites M-II and M-IV in blood and the concentration of the tacrolimus (that is a medical agent to be measured) in blood.

A model in which the quantitative values of tacrolimus, M-II and M-IV are calculated is shown with reference to the aforementioned document (FIG. 5). In this model, values (10 ng/ml) measured in the immunological method and relative ratios (tacrolimus with a relative ratio of 100%; M-II with a relative ratio of 20%; and M-IV with a relative ratio of 10%) of peak areas of the components subjected to an MS measurement are given here as one example to explain the principle.

FIG. 5 shows a process to calculate corrected quantitative values in the MS measurement of the captured components. It is assumed that a value measured by quantifying the tacrolimus in the patient's specimen using the immunological method is 10 ng/ml. A method for calculating the concentration ratios of the tacrolimus, the M-II and the M-IV on the basis of a chromatograph obtained when the aforementioned measured value is 10 ng/ml is shown in FIG. 5 on the assumption that the relative value of the peak area associated with the tacrolimus is 100%, the relative value of the peak area associated with the M-II is 20% and the relative value of the peak area associated with the M-IV is 10%. The concentration ratios of the three components (tacrolimus, M-II and M-IV) captured by the immunological method are 76.9%, 15.4% and 7.7%, respectively. When the quantitative value obtained by quantifying the tacrolimus using the immunological method is 10 ng/ml, the proportions of the tacrolimus, M-II and M-IV are 7.7 ng/ml, 1.5 ng/ml and 0.8 ng/ml, respectively, on the basis of the concentration ratios of the components. Thus, the concentration of the tacrolimus in the sample, which is measured by the immunological method, is not 10 ng/ml. This calculation shows that more precisely the concentration of the tacrolimus is 7.7 ng/ml, which is a value obtained by subtracting the values estimated for the components that cause the cross-reactivity from the value measured by the immunological method.

In this manner, the quantitative values of the captured components are calculated from the proportions of the components captured in the MS measurement. This calculation allows the quantitative values to be calculated from data other than the sum of the plurality of components causing the cross-reactivity that is a problem in the immunological method. In addition, this calculation makes it possible to calculate the quantitative value of each of the components by calculating, through the MS measurement, the proportions of the components captured by the immunological method and calculating the ratios of the values measured in the immunological method. Any internal standard substance necessary to measure quantitative values in the MS method is not used in this case.

In addition, the quantitative values of the components captured by the immunological method are not only calculated but also used as indexes to determine whether the state of the patient is normal or abnormal on the basis of disassociation from a standard profile (for example, an average disease-specific profile, a past history profile of the patient or the like) that is a criterion for the state of the patient and is based on profiles (patterns of the proportions) of the components, for example.

This means that a technique for planning safe and effective administration of drugs is provided by identifying and understanding the concentrations of the components (to be measured) in blood and the concentrations of the metabolites and the like in blood, where the metabolites and the like have effects as medicine.

For example, the abovementioned technique is executed by an automatic processing system. It is considered that such a system is loaded with software that performs a necessary measurement by selecting the name of a medical agent, a medical agent group, a disease or the like and systematically and automatically calculates information obtained by the measurement.

Figure 6:
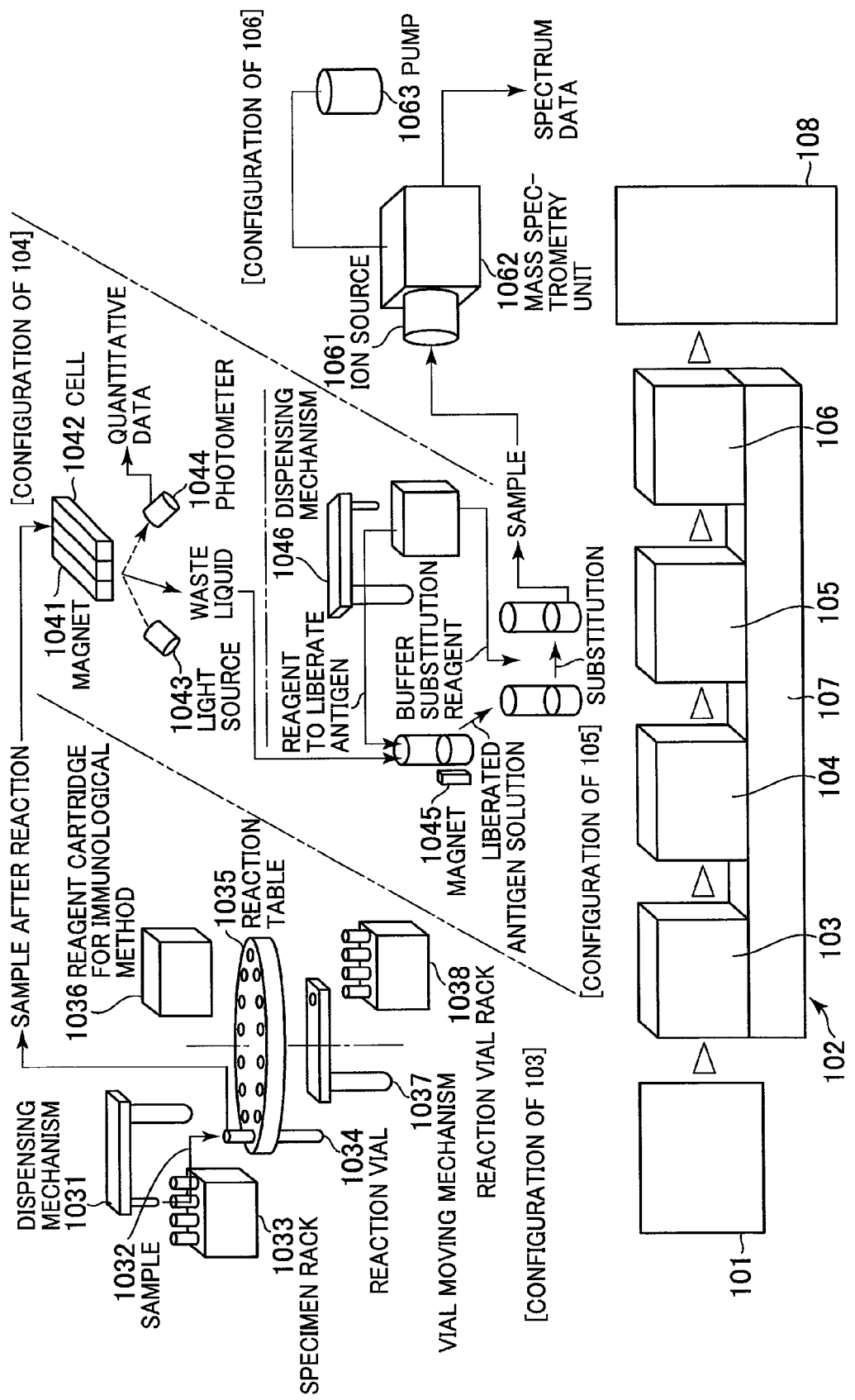
FIG. 6 is a diagram showing an example of a configuration of the sample immunoanalytical system shown in FIG. 1.

FIG. 6 is a diagram showing an example of a configuration of the system 102 for immunoanalysis of samples shown in FIG. 1.

In the immunological pretreatment device 103 shown in FIG. 6, a sample 1032 that is stored on a specimen rack 1033 is dispensed into a reaction vial 1034 by a dispensing mechanism 1031. The reaction vial 1034 is arranged at a reaction table 1035. In addition, a reagent that is stored in a reagent cartridge 1036 for the immunological method is dispensed into the reaction vial 1034. The reaction vial 1034 is moved by a vial moving mechanism 1037 from a reaction vial rack 1038 to the reaction table 1035.

In the immunological photometric detection system 104, the sample that is supplied from the immunological pretreatment device 103 passes through a cell 1042 provided with a magnet 1041 and is irradiated with light emitted from a light source 1043. The sample is then subjected to light detection by a photometer 1044 so that quantitative data is detected by the photometer 1044.

A waste liquid from the immunological photometric detection system 104 is supplied to the mass spectrometric pretreatment device 105.

In the mass spectrometric pretreatment device 105, the waste liquid from the immunological photometric detection system 104 is mixed with a reagent to liberate an antigen dispensed by a dispensing mechanism 1046, and a liberated antigen solution results under the action of a magnet 1045. The waste liquid is subjected to a substitution with a buffer substitution reagent. The waste liquid subjected to the substitution is supplied to the mass spectrometric detection system 106.

The mass spectrometric detection system 106 includes an ion source 1061, a mass spectrometry unit 1062 and a vacuum pump 1063. The sample is subjected to mass spectrometry by the mass spectrometric detection system 106 so that spectrum data 108 is obtained.

Figure 7:
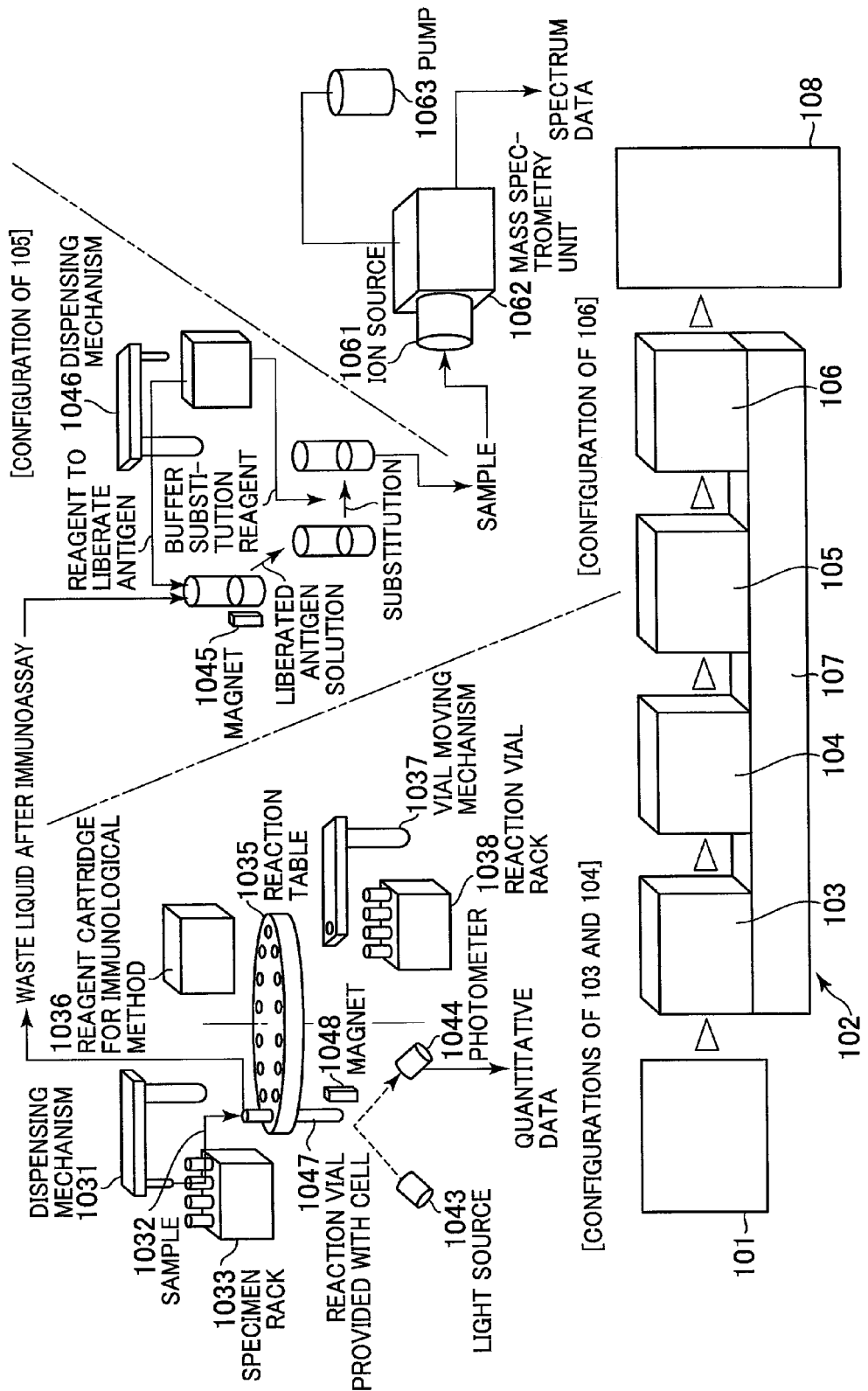
FIG. 7 is a diagram showing another example of the configuration of the sample immunoanalytical system shown in FIG. 1.

FIG. 7 is a diagram showing another example of the configuration of the immunoanalytical system 102 shown in FIG. 1.

The configurations of the immunological pretreatment device 103, the mass spectrometric pretreatment device 105 and the mass spectrometric detection system 106, which are shown in the example of FIG. 7, are the same as those shown in the example of in FIG. 6. However, the configuration of the immunological photometric detection system 104 shown in the example of in FIG. 7 is different from that shown in the example of in FIG. 6.

In the immunological photometric detection system 104 shown in FIG. 7, a magnet 1048 is arranged in the vicinity of a reaction vial 1047 provided with a cell, while the reaction vial 1047 is arranged at the reaction table 1035. A reagent and a sample, which are stored in the reaction vial 1047 provided with the cell, are irradiated with light emitted from the light source 1043 so that quantitative data is measured by the photometer 1044.

Then, a waste liquid from the immunological photometric detection system 104 is supplied to the mass spectrometric pretreatment device 105.

Figure 8:
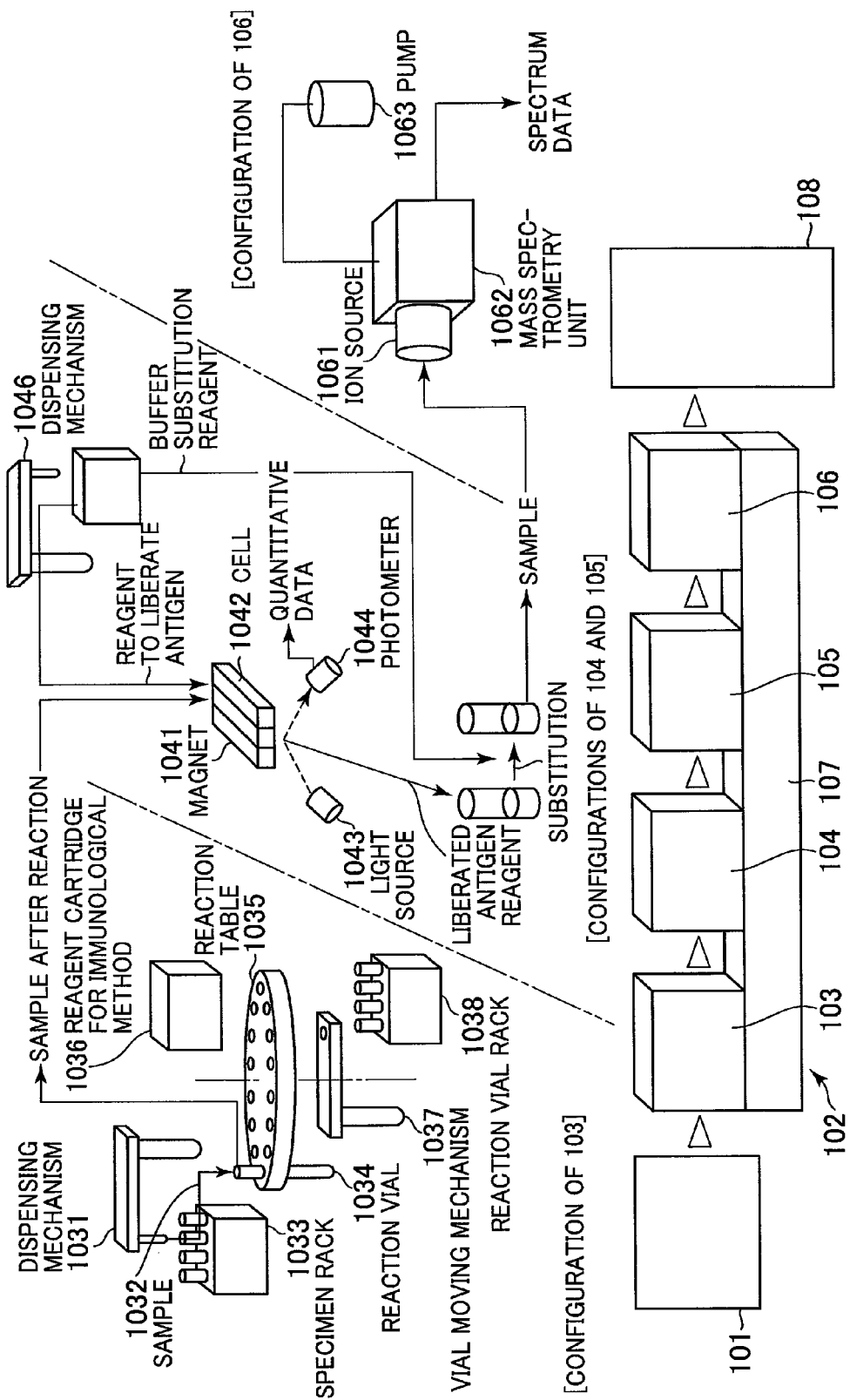
FIG. 8 is a diagram showing still another example of the configuration of the sample immunoanalytical system shown in FIG. 1.

FIG. 8 a diagram showing still another example of the configuration of the immunoanalytical system 102 shown in FIG. 1.

The configurations of the immunological pretreatment device 103 and the mass spectrometric detection system 106, which are shown in the example of FIG. 8, are the same as those shown in the example of FIG. 6. However, the configurations of the immunological photometric detection system 104 and the mass spectrometric pretreatment device 105, which are shown in the example of FIG. 8, are different from those shown in the example of FIG. 6.

In the immunological photometric detection system 104 shown in FIG. 8, the incubated sample from the immunological pretreatment device 103 is supplied to the cell 1042 together with the reagent to liberate the antigen dispensed by the dispensing mechanism 1046, while the magnet 1041 is arranged at the cell 1042.

The sample supplied to the cell 1042 is irradiated with light emitted from the light source 1043 and subjected to light detection by the photometer 1044 so that quantitative data is detected.

Then, a waste liquid from the immunological photometric detection system 104 is supplied to the mass spectrometric pretreatment device 105. In the mass spectrometric pretreatment device 105, the waste liquid is subjected to a substitution with a buffer substitution reagent and then supplied to the mass spectrometric detection system 106.

Figure 9:
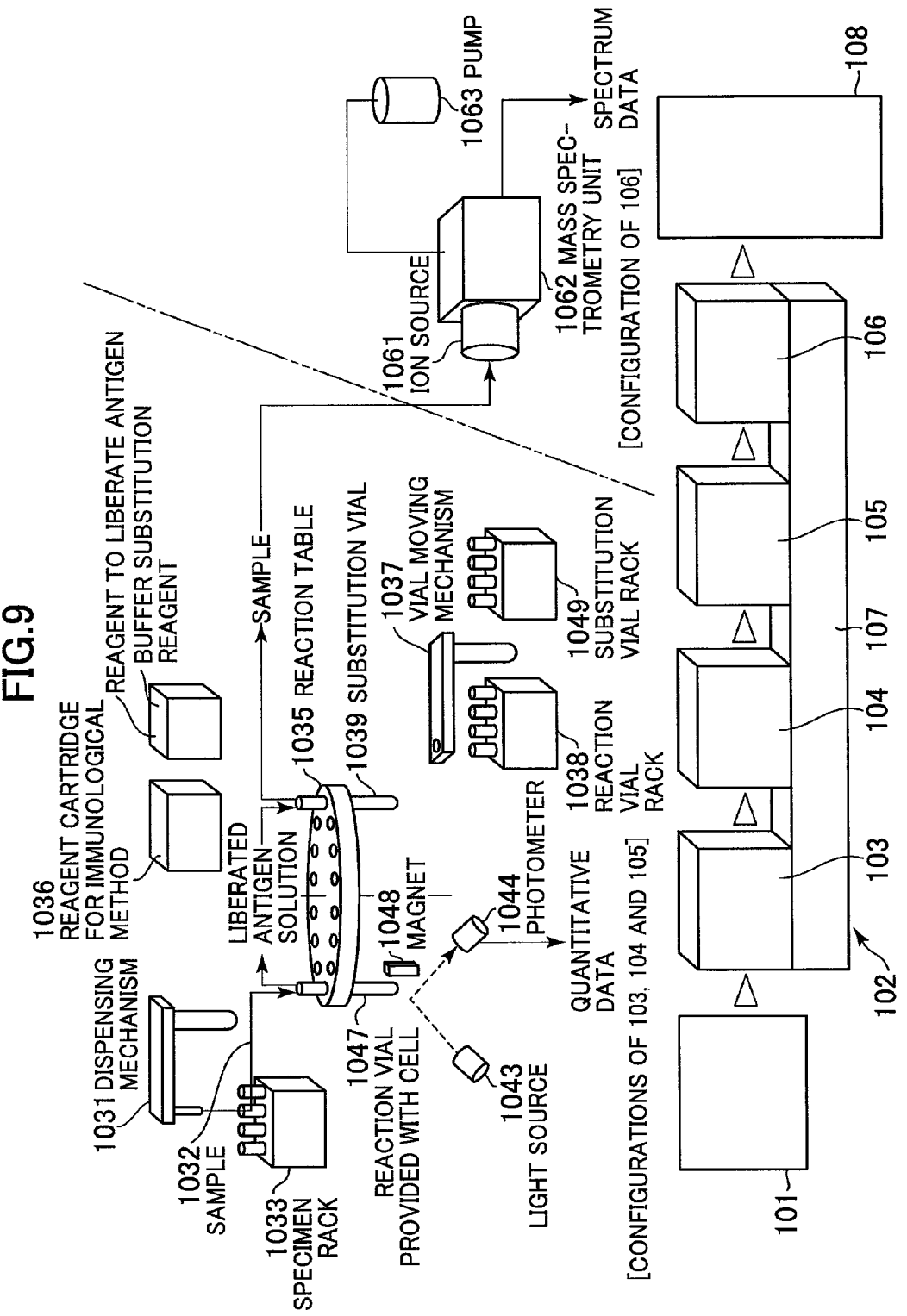
FIG. 9 is a diagram showing still another example of the configuration of the sample immunoanalytical system shown in FIG. 1.

FIG. 9 is a diagram showing still another example of the configuration of the immunoanalytical system 102 shown in FIG. 1.

The configuration of the mass spectrometric detection system 106, which is shown in the example of FIG. 9, is the same as that shown in the example of FIG. 6. However, the configurations of the immunological pretreatment device 103, the immunological photometric detection system 104 and the mass spectrometric pretreatment device 105, which are shown in the example of FIG. 9, are different from those shown in the example of FIG. 6.

In the immunological pretreatment device 103, the immunological photometric detection system 104, and the mass spectrometric pretreatment device 105 which are shown in FIG. 9, the sample that is held by the specimen rack 1033 is dispensed into the reaction vial 1047 provided with the cell by a dispensing mechanism 1031, while the reaction vial 1047 is arranged at the reaction table 1035. A reagent that is stored in the reagent cartridge for the immunological method is dispensed into the reaction vial 1047. The reaction vial 1047 is moved by the vial moving mechanism 1037 from the reaction vial rack 1038 to the reaction table 1035.

The magnet 1048 is arranged in the vicinity of the reaction vial 1047 provided with the cell. The sample stored in the reaction vial 1047 is irradiated with light emitted from the light source 1043 so that quantitative data is obtained by the photometer 1044.

A substitution vial 1039 is moved from a substitution vial rack 1049 by the vial moving mechanism 1037 and arranged at the reaction table 1035. The reagent to liberate the antigen is supplied into the sample stored in the reaction vial 1047 provided with the cell. The liberated antigen solution is supplied from the reaction vial 1047 to the substitution vial 1039. The solution that is subjected to a substitution with the buffer substitution reagent is supplied to the mass spectrometric detection system 106.

The immunoanalytical systems 102 shown in FIGS. 6 to 9 can each exhibit the aforementioned effect of the present invention.

Second Embodiment

Next, the second embodiment of the present invention is described.

The second embodiment of the present invention describes an example in which a sample to be subjected to light detection in the immunological method is used for a detection of a component in mass spectrometry. In the example, sandwich assay using a secondary antibody in the immunological method is not applied, and a substance (to be measured) captured by a primary antibody and substances with similar structures such as a metabolite causing cross-reactivity are quantified by mass spectrometry.

Figure 10:
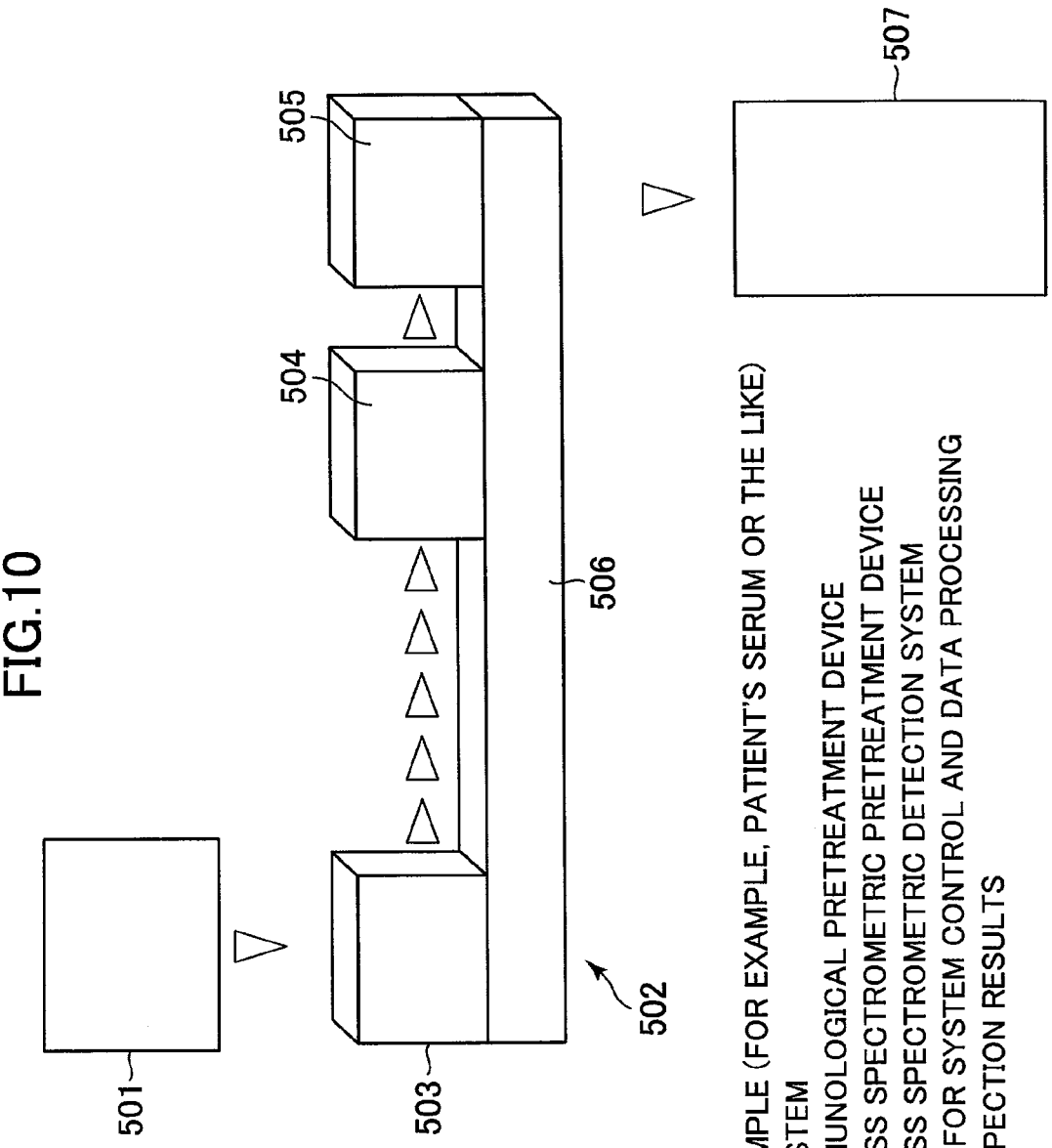
FIG. 10 is a diagram showing an outline configuration of an entire sample immunoanalytical system according to a second embodiment of the present invention and showing the flow of a measurement.

FIG. 10 is a diagram showing an outline configuration of an entire system 502 for immunoanalysis of samples according to the second embodiment of the present invention and showing the flow of a measurement. Operations of the entire immunoanalytical system 502 are controlled by a personal computer 506 for system control and data processing.

Figure 11:
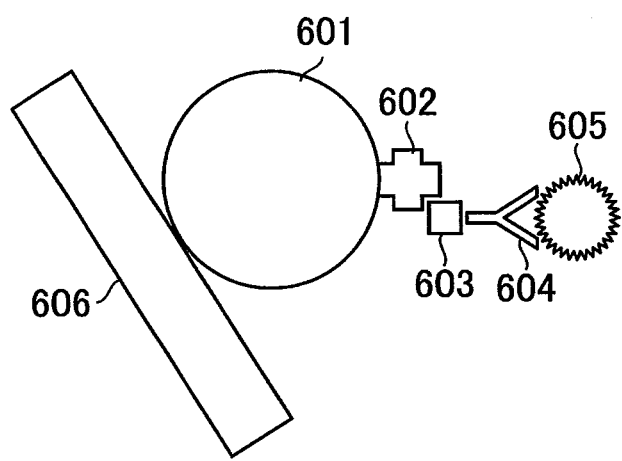
FIG. 11 is a diagram showing an application in a pretreatment for the immunological method.

Referring to FIGS. 10 and 11, an immunological pretreatment device 503 subjects to pretreatment a component that is to be measured and is contained in a sample 501 (for example, whole blood, blood plasma, a serum, urine or the like) derived from a biological body, according to an automatic immunoanalytical method. The pretreated component to be measured is selectively captured by an antibody 604 that specifically recognizes the component 605. The antibody 604 is bound with a magnetic particle by avidin-biotin binding (602-603) or the like in advance. A magnetic particle 601 captures the target analyte component (to be measured) through an antibody 604 and is collected by a magnetic force of a magnetic body 606. Then, an unnecessary element or the like in the ambient solution around the magnetic particle 601 is washed away.

Since this captured component includes not only a value of the component to be measured but also a substance (such as a metabolite derived from the component) that has a structure similar to that of the component and thereby causes cross-reactivity, the captured component is not necessarily a single component to be recognized by the antibody. Therefore, proportions (relative ratios) of components contained in the captured component are calculated by mass spectrometry.

As shown in FIG. 12, a mass-spectrometric pretreatment device 504 collects a component 305 captured by the antigen-antibody reaction. For example, a product formed by the antigen-antibody reaction is subjected to an acid treatment, an alkaline treatment, an ionic strength treatment and the like so that the antigen (component 305 to be measured) is disassociated from the antigen-antibody bond and liberated from an the antibody 304. Magnetic beads 301 are collected under a magnetic force again and a supernatant is collected. After subjected to a solvent substitution, the supernatant is supplied to a mass spectrometric detection system 505.

Depending on properties of the component to be measured, a component that is contained in the supernatant may be separated from the supernatant by a chromatographic method such as size fractionation or fractionated by enzyme digestion when necessary.

The mass spectrometric detection system 505 subjects to mass spectrometry components that are contained in the supernatant. A signal intensity and a peak area are calculated from each of the components on the basis of the chromatograph obtained and the relative ratios of the components are calculated. Quantitative values of the components may be separately calculated using an internal standard substance.

This means that a technique for planning safe and effective administration is provided by identifying and understanding the concentrations of the components (to be measured) in blood and the concentrations of the metabolites and the like in blood, where the metabolites and the like have effects as medicine.

For example, the abovementioned technique is executed by an automatic processing system. It is considered that such a system is loaded with software that performs a necessary measurement by selecting the name of a therapeutic agent, a therapeutic agent group, a disease or the like, and systematically and automatically calculates information obtained by the measurement.

Figure 13:
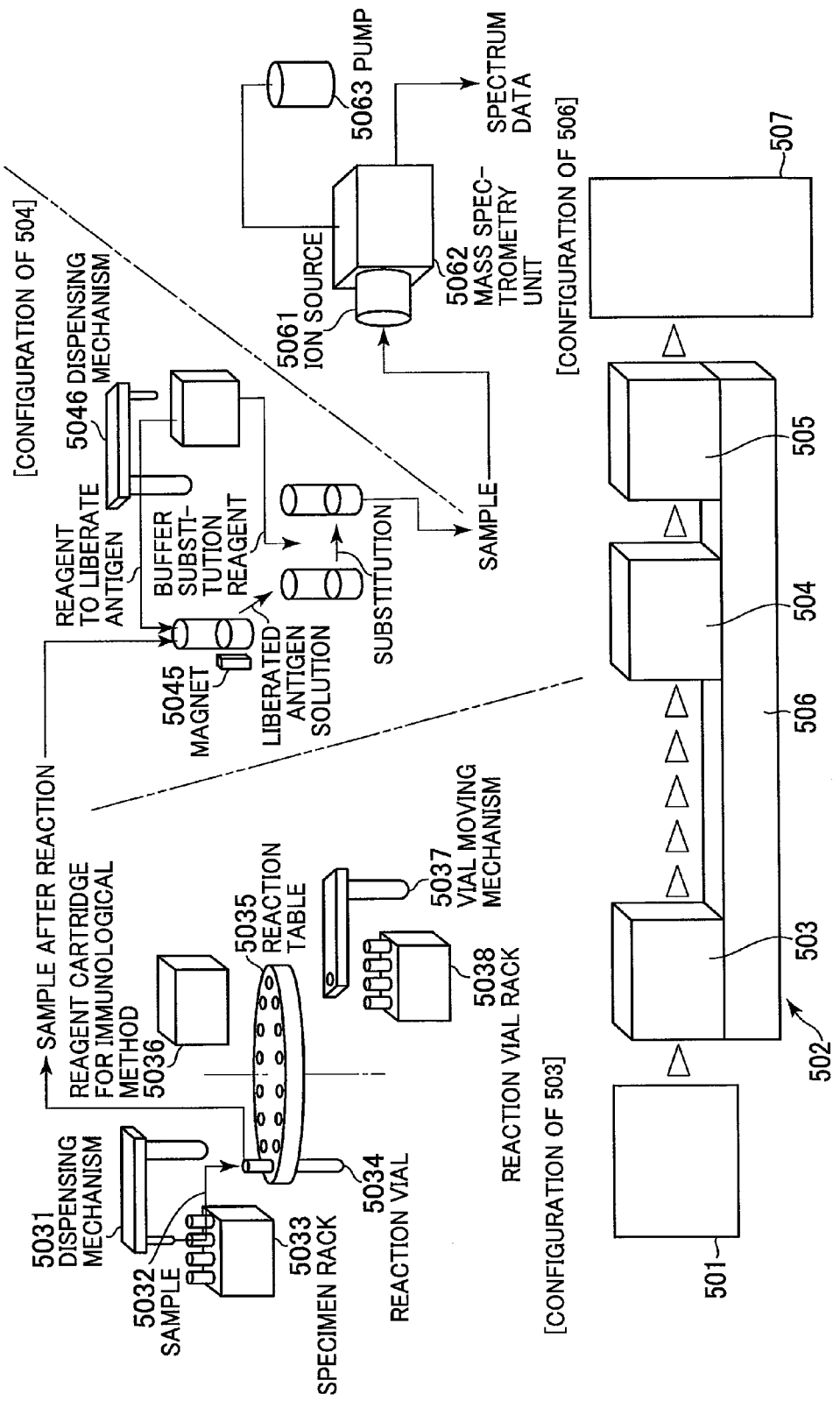
FIG. 13 is a diagram showing an example of a configuration of the sample immunoanalytical system shown in FIG. 10.

FIG. 13 is a diagram showing a configuration of the immunoanalytical system 502 shown in FIG. 10.

In the immunological pretreatment device 503 shown in FIG. 13, a sample 5032 that is stored on a specimen rack 5033 is dispensed into a reaction vial 5034 by a dispensing mechanism 5031. The reaction vial 5034 is arranged at a reaction table 5035. In addition, a reagent that is stored in a reagent cartridge 5036 for the immunological method is dispensed into the reaction vial 5034. The reaction vial 5034 is moved by a vial moving mechanism 5037 from a reaction vial rack 5038 to the reaction table 5035.

In the mass spectrometric pretreatment device 504, a solution that is obtained after an immunological reaction process and supplied from the immunological pretreatment device 503 is mixed with a reagent to liberate an antigen dispensed by a dispensing mechanism 5046, and a liberated antigen solution is obtained by an action of a magnet 5045. The sample is subjected to a substitution with a buffer substitution reagent. The sample subjected to the substitution is supplied to the mass spectrometric detection system 505.

The mass spectrometric detection system 505 includes an ion source 5061, a mass spectrometry unit 5062 and a vacuum pump 5063. The sample is subjected to mass spectrometry by the mass spectrometric detection system 505 so that spectrum data 507 is obtained.

Figure 14:
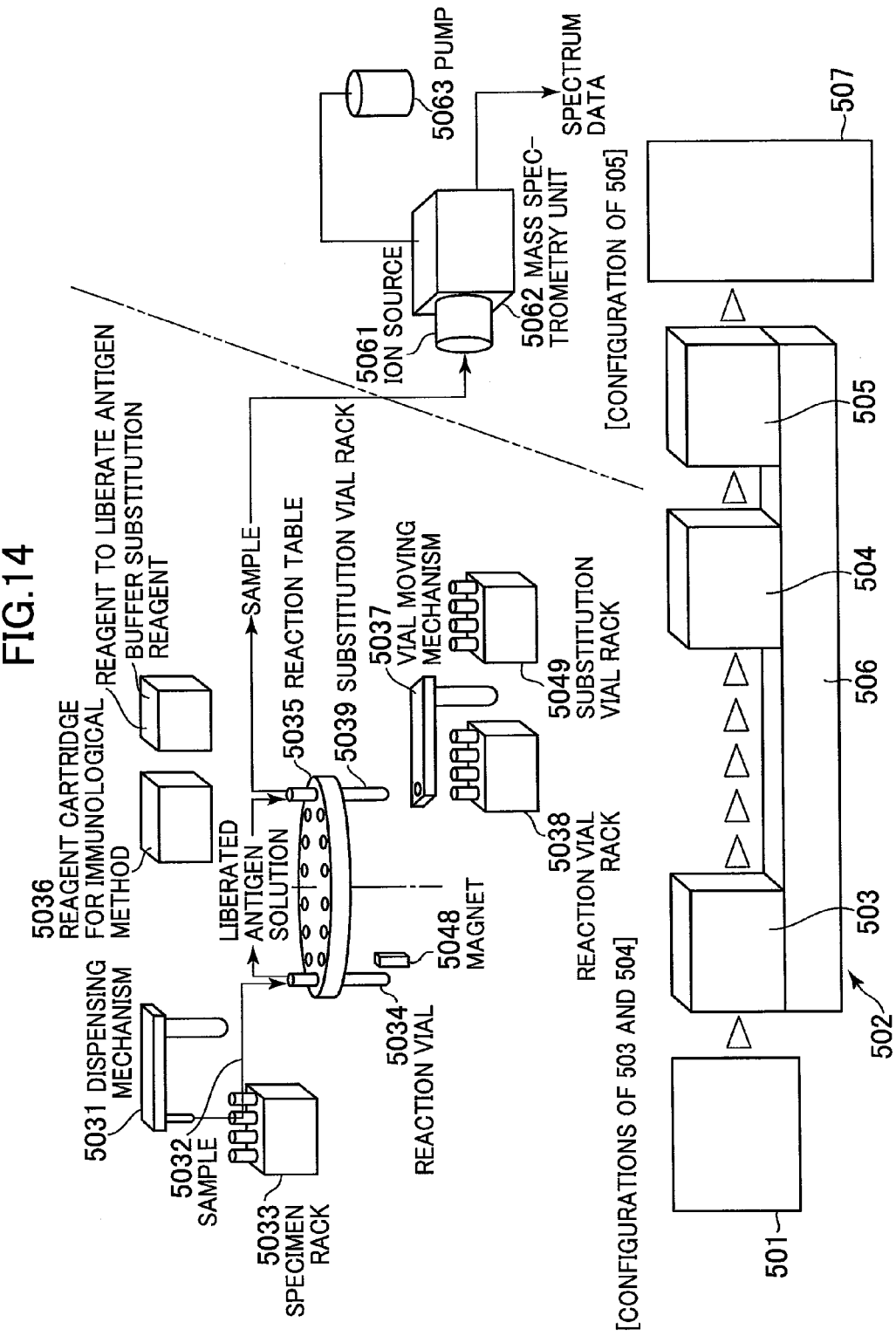
FIG. 14 is a diagram showing another example of the configuration of the sample immunoanalytical system shown in FIG. 10.

FIG. 14 is a diagram showing another example of the configuration of the immunoanalytical system 502 shown in FIG. 10.

In the immunological pretreatment device 503 and the mass spectrometric pretreatment device 504 shown in FIG. 14, the sample that is held by the specimen rack 5033 is dispensed into the reaction vial 5034 by the dispensing mechanism 5031, while the reaction vial 5034 is arranged at the reaction table 5035. A reagent that is stored in the reagent cartridge 5036 for the immunological method is dispensed in the reaction vial 5034. The reaction vial 5034 is moved by the vial moving mechanism 5037 from the reaction vial rack 5308 to the reaction table 5035.

A magnet 5048 is arranged in the vicinity of the reaction vial 5034. A substitution vial 5039 is moved from a substitution vial rack 5049 by the vial moving mechanism 5037 and is arranged at the reaction table 5035. A reagent to liberate an antigen is supplied in the sample stored in the reaction vial 5034. The liberated antigen solution is supplied from the reaction vial 5034 to the substitution vial 5039. The solution is subjected to a substitution with a buffer substitution reagent and supplied to the mass spectrometric detection system 505.

Third Embodiment

For example, after a component captured by the immunological method is liberated from a capturing substance (for example, magnetic beads) contained in a reagent for the immunological method, a supernatant (reaction solution) formed when the magnetic beads are captured by using the magnet may be subjected to a solid-phase extraction process so that only the component to be measured is extracted.

A solid-phase extraction agent is selected on the basis of properties of the component to be measured. For example, if the molecular size, hydrophobicity or Tonicity of the component to be measured is different from that of a reagent to detect light emission, it is possible to separately collect the component to be measured and the reagent to detect light emission by using an extraction mode such as size fractionation, reversed-phase separation, ion-exchange separation or the like. In order to perform the solid-phase extraction process, the composition, concentration, pH and the like of the supernatant (reaction solution) may be changed when necessary.

Figure 15:
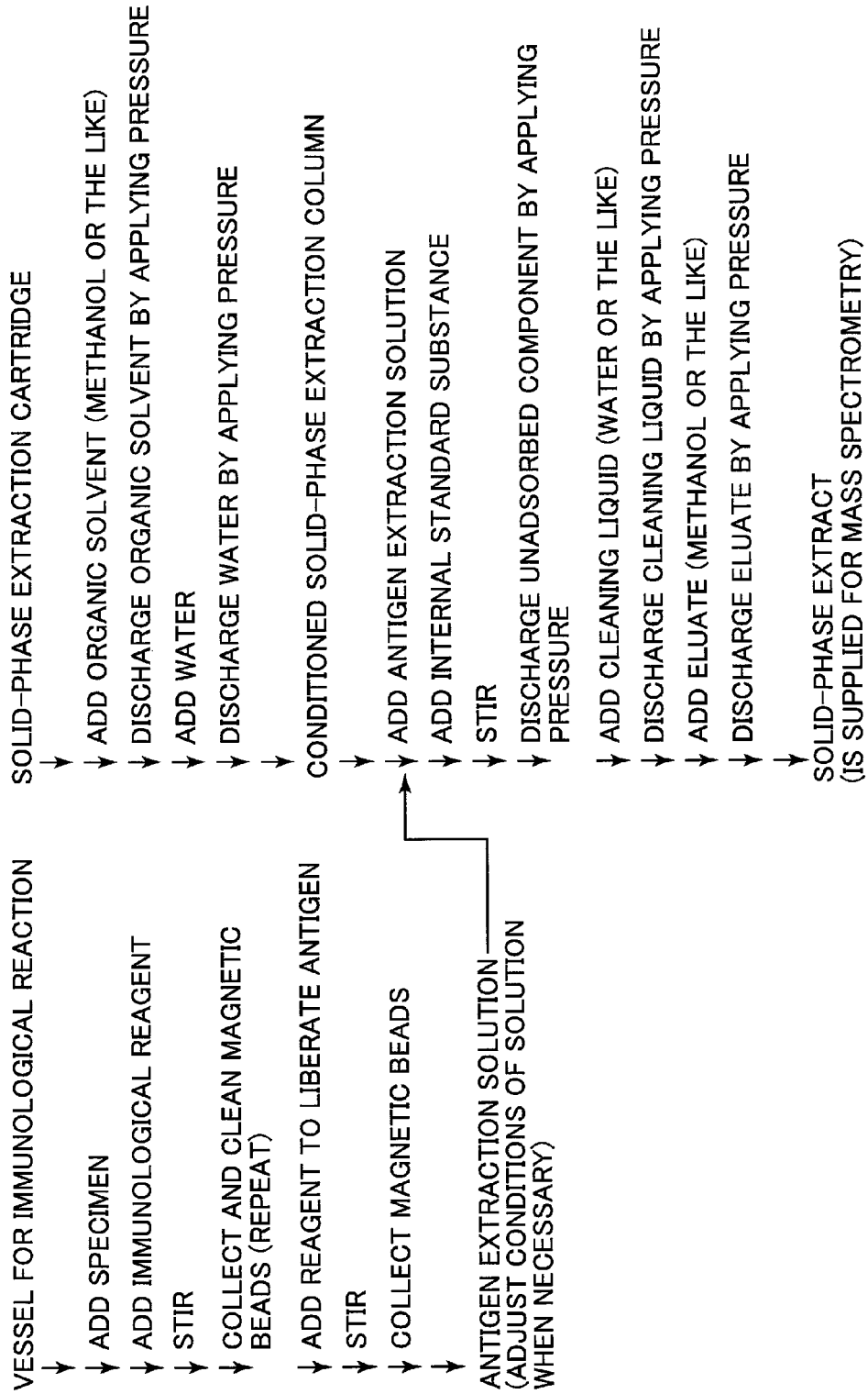
FIG. 15 is a flowchart of an immunological reaction process and a solid-phase extraction process.

The immunological reaction process and the solid-phase extraction process are performed in the sequence shown in FIG. 15.

Figure 16:
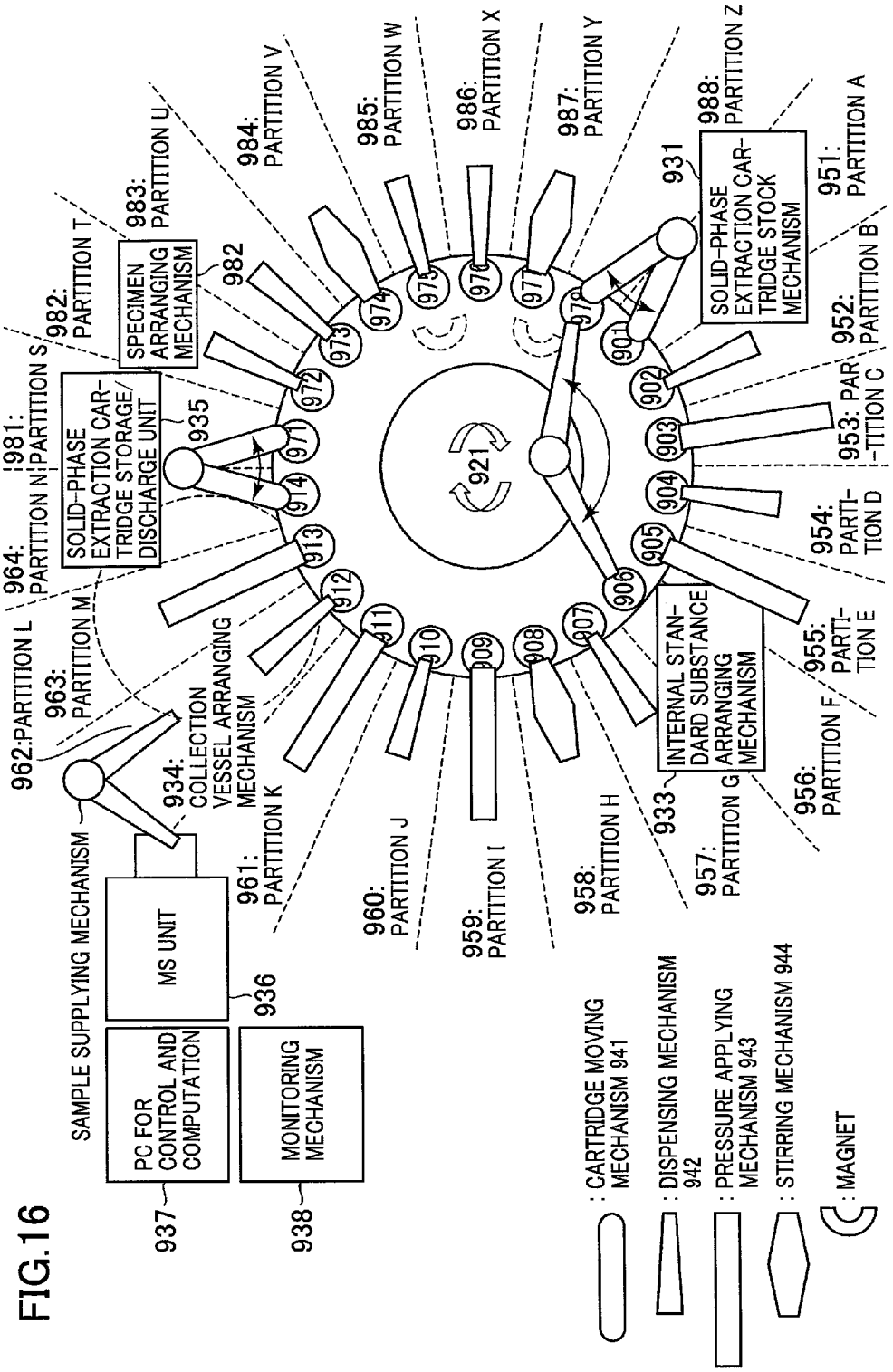
FIG. 16 is a top view of a configuration of a system that is related to the solid-phase extraction process.

The processes can be automatically performed by arranging a mechanism for performing the immunological reaction process and the solid-phase extraction process on a rotating table, where each of partitions on a turn table executes either one of the immunological process or the solid phase extraction, for example (FIG. 16). Next, the following describes the flow of the immunological reaction process and the solid-phase extraction process when the processes are automatically performed on the same turn table.

FIG. 15 shows the flow of the immunological reaction process and the solid-phase extraction process. The immunological reaction process includes a process of capturing a component that is to be measured and is contained in a specimen by an antigen-antibody reaction using an immunological reagent, a process of cleaning and removing an unnecessary element, and a process of liberating the component to be measured from the immunological reagent. The solid-phase extraction process includes a process of conditioning a solid-phase extraction filler agent using an organic solvent and $H_2O$, a process of supplying the sample into the solid-phase extraction agent, a process of cleaning and removing an unnecessary element nonspecifically adsorbed on the solid-phase extraction filler agent, and a process of eluting and collecting a target component specifically adsorbed on the solid-phase extraction filler agent. An extracted material is supplied to the mass spectrometric device or the like and can be used for a clinical inspection by identifying or quantifying a component contained in the extracted material, for example.

When the immunological reaction process and the solid-phase extraction process are performed on the same turn table, the process of conditioning the solid-phase extraction agent is performed in parallel during the immunological reaction process. In this case, it is necessary to match the timing of obtaining a solution (antigen extraction solution) by roughly purifying the component (to be measured) obtained by the immunological reaction with the timing of completion of the conditioning of the solid-phase extraction agent. For example, as shown in FIG. 18, it is assumed that the immunological reaction process starts to be performed on a sample 1 in a partition S as the first step. At the same time when the immunological reaction process reaches a partition U, the solid-phase extraction process simultaneously starts to be performed on the sample in a partition A. The antigen extraction solution obtained when the immunological reaction process reaches a partition Z is added to a partition F in which the solid-phase extraction process is performed. By adding the antigen extraction solution to the partition F, the immunological reaction process of the sample 1 is completed. Only the solid-phase extraction process is continuously performed on the sample in remaining partitions.

The process is performed on a sample 2 and the subsequent samples in the same manner. The process starts when a previous sample moves to a partition T and the partition S is vacant.

Thus, in order to move the antigen extraction solution from the partition Z to the partition F, it is preferable that the same dispensing mechanism be used.

In the solid-phase extraction process, in order to cause the reagent, the sample or the like to flow through the solid-phase extraction agent, pressure is applied (in a pressure application process on the upstream side of a solid-phase extraction cartridge or in a negative pressure application process on the downstream side of the solid-phase extraction cartridge). A solution, which passes through the solid-phase extraction agent and flows out, is collected and supplied for analysis, in which case solution only obtained in the elution and collection process (the last process) is used. Solutions that are discharged from other processes are treated as waste liquids.

FIG. 16 shows an example of a top view of a configuration of a system that automates the solid-phase extraction process when a separate type solid-phase extraction cartridge is used in which a solid-phase extraction column is provided separately from a collecting device. In order to achieve the ability to randomly select the target analytes for each of specimens to be measured in a clinical inspection or the like or for each of inspection items, immunological reaction process vessels are concentrically arranged in eight partitions of a turn table (or arranged at cartridge holding units 971 to 978 located in partitions S to Z), respectively. Solid-phase extraction cartridges are concentrically arranged in 14 partitions (or arranged at cartridge holding units 901 to 914 located in partitions A to N), respectively. The processes that are included in the immunological reaction process and the solid-phase extraction process are sequentially performed on the same circumference in parallel according to the flow shown in FIG. 15 and the sequence shown in FIG. 18. Detailed operational procedures are described below using concentration measurement of a medicinal agent in blood as an example. The system includes a monitoring mechanism (938) that monitors the states of the processes. A PC (937) controls the entire system and performs a calculation such as data analysis.

The immunological reaction process is performed according to the following procedures.

First, an immunological reaction vessel is transported by a cartridge moving mechanism to the cartridge holding unit (971) located in the partition S on the turn table.

Next, the immunological reaction vessel is moved to the cartridge holding unit (972) located in the partition T on the turn table, and a specimen is added into the immunological reaction vessel.

Then, the immunological reaction vessel is moved to the cartridge holding unit (973) located in the partition U on the turn table, and an immunological reagent is added into the immunological reaction vessel.

Then, the immunological reaction vessel is moved to the cartridge holding unit (974) located in the partition V on the turn table, and the specimen and the reagent that are contained in the vessel are stirred.

Then, the immunological reaction vessel is moved to the cartridge holding unit (975) located in the partition W on the turn table, and magnetic beads that have captured an antigen contained in the specimen are collected by a magnet.

The reaction solution is removed while the magnetic beads are cleaned by a cleaning liquid. After the cleaning, the cleaning liquid is removed.

Then, the immunological reaction vessel is moved to the cartridge holding unit (976) located in the partition X on the turn table, a reagent to liberate the antigen is added.

Then, the immunological reaction vessel is moved to the cartridge holding unit (977) located in the partition Y on the turn table, the solution stored in the vessel is stirred.

Then, the immunological reaction vessel is moved to the cartridge holding unit (978) located in the partition Z on the turn table, magnetic beads are collected by the magnet, and the solution containing the liberated antigen is collected and supplied to a conditioned solid-phase extraction agent located in the partition F. The composition (condition) of the antigen extraction solution may be adjusted when necessary. In addition, the used immunological reaction vessel is discarded.

The solid-phase extraction process is performed in parallel with the immunological reaction process according to the following procedures.

First, in synchronization with the action of the immunological reaction process reaching the partition U, a solid-phase extraction cartridge moving mechanism (941) transports a single solid-phase extraction cartridge from a solid-phase extraction cartridge stock mechanism (931) to the cartridge holding unit (901) located in the partition A on the turn table (921). This solid-phase extraction cartridge is called a C1 for convenience purpose in the following description.

Then, the turn table (921) rotates clockwise a distance corresponding to a single partition so that the C1 moves to the cartridge holding unit (902) located in the partition B. An organic solvent dispensing mechanism (942) for conditioning dispenses a certain amount of an organic solvent (for example, 100% methanol) in the C1.

Then, the turn table (921) rotates clockwise a distance corresponding to a single partition so that the C1 moves to the cartridge holding unit (903) located in the partition C. Pressure is applied to the C1 by a pressure applying mechanism (943) so that the organic solvent is made to flow through the solid-phase extraction agent. A waste liquid is collected by a drain, a waste liquid collection vessel or the like and then discarded.

Then, the turn table (921) rotates clockwise a distance corresponding to a single partition so that the C1 moves to the cartridge holding unit (904) located in the partition D. The $H_2O$ dispensing mechanism (942) for conditioning dispenses a certain amount of $H_2O$ in the C1.

Then, the turn table (921) rotates clockwise a distance corresponding to a single partition so that the C1 moves to the cartridge holding unit (905) located in the partition E. Pressure is applied to the C1 by the pressure applying mechanism (943) so that the organic solvent is made to flow through the solid-phase extraction agent. A waste liquid is collected by the drain, the waste liquid collection vessel or the like and then discarded.

Then, the turn table (921) rotates clockwise a distance corresponding to a single partition so that the C1 moves to the cartridge holding unit (906) located in the partition F. The antigen extraction solution collected in the partition Z is supplied to the C1.

Then, the turn table (921) rotates clockwise a distance corresponding to a single partition so that the C1 moves to the cartridge holding unit (907) located in the partition G. The internal standard substance dispensing mechanism (942) collects a certain amount of an internal standard substance from an internal standard substance vessel arranged at an internal standard substance dispensing position of an internal standard substance arranging mechanism (933) and dispenses the internal standard substance in the C1.

Then, the turn table (921) rotates clockwise a distance corresponding to a single partition so that the C1 moves to the cartridge holding unit (908) located in the partition H. A stirring mechanism (944) stirs the specimen and the internal standard substance in the C1.

Then, the turn table (921) rotates clockwise a distance corresponding to a single partition so that the C1 moves to the cartridge holding unit (909) located in the partition I. Pressure is applied to the C1 by the pressure applying mechanism (943) so that a mixed solution containing the specimen and the internal standard substance is made to flow through the solid-phase extraction agent. A waste liquid is collected by the drain, the waste liquid connection vessel or the like and then discarded.

Then, the turn table (921) rotates clockwise a distance corresponding to a single partition so that the C1 moves to the cartridge holding unit (910) located in the partition J. The cleaning liquid dispensing mechanism (942) dispenses a certain amount of a cleaning liquid in the C1.

Then, the turn table (921) rotates clockwise a distance corresponding to a single partition so that the C1 moves to the cartridge holding unit (911) located in the partition K. Pressure is applied to the C1 by the pressure applying mechanism (943) so that the cleaning liquid is made to flow through the solid-phase extraction agent. A waste liquid is collected by the drain, the waste liquid collection vessel or the like and then discarded.

Then, the turn table (921) rotates clockwise a distance corresponding to a single partition so that the C1 moves to the cartridge holding unit (912) located in the partition L. The eluate dispensing mechanism (942) dispenses a certain amount of an eluate in the C1.

Then, the turn table (921) rotates clockwise a distance corresponding to a single partition so that the C1 moves to the cartridge holding unit (913) located in the partition M. Pressure is applied to the C1 by the pressure applying mechanism (943) so that the cleaning liquid flows through the solid-phase extraction agent. FIG. 17 is a side view of the configuration of the system when the partition M is viewed. The eluate that is discharged from the solid-phase extraction cartridge (1001) C1 is collected in a collection vessel (1002) that stands by and is located directly under a C1 discharge port located above a collection vessel arranging mechanism (934, 1006). In addition, in order to cause the process to proceed a mass spectrometry process, the collection vessel (1002) that contains the collected eluate is moved and located at a predetermined position of the collection vessel arranging mechanism (934, 1006). After that, the eluate is supplied to a mass spectrometry unit (936, 1007) in an online or offline mode so that the mass spectrometry unit (936, 1007) quantifies a target component contained in the eluate while separating the target component from the eluate.

As an example in which the sample is supplied to the MS in the offline mode, it is considered that the dispensing mechanism absorbs a necessary amount of an extracted material and directly or indirectly (for example, a flow injection method) supplies the extracted material into an ion source of the MS.

Then, the turn table (921) rotates clockwise a distance corresponding to a single partition so that the C1 moves to the cartridge holding unit (914) located in the partition N. The solid-phase extraction cartridge moving mechanism (941) collects the C1 from the turn table (921) and discards the C1 in a cartridge discarding unit (935).

The aforementioned process is a series of the operations performed on the turn table. Next, when the turn table (921) rotates a distance corresponding to a single partition in the clockwise direction, the cartridge holding unit that is vacant after the discarding of the C1 returns to the partition A (951) and the solid-phase extraction process is completed for one process.

After the solid-phase extraction process, the collection vessel can be removed from the turn table by a collection arm and stored, instead of being discarded. In order to measure the extracted material again, the stored collection vessel is arranged in a vacant partition of the turn table. For example, when the collection vessel is managed using a barcode, the barcode is automatically recognized and the collection vessel is moved to a position at which the collection vessel is loaded on the MS so that the extracted material is measured again.

A lid may be placed on an upper end of the stored collection vessel in order to prevent the extracted material from being dry when necessary. Even when the extracted material becomes dry, the extracted material can be measured again by dissolving the extracted material with a solvent. In this case, the amount of the added solvent is controlled to a value obtained by subtracting an amount consumed for the measurement from a monitored value of a liquid surface (or amount) of the material extracted during the solid-phase extraction process, for example.

For example, in the above description, a new solid-phase extraction cartridge (1001) that is called a C2 (for convenience) is introduced in a vacant cartridge holding unit that is located in the partition A after the C1 is moved to the cartridge holding unit (902) located in the partition B and a process starts to be performed on the second specimen in the C2 while being delayed by a time corresponding to a single partition (operation). The third and later specimens are processed after the C2 in the same manner. Thus, the process is performed in sequence in parallel on 14 specimens on the turn table (921). The 14 specimens correspond to the number of the partitions. For a re-inspection, the process is performed in the same manner.

The aforementioned effect of the present invention can be obtained by the sample immunoanalytical system 502 shown in each of FIGS. 13 and 14.

The present invention is effective to increase the accuracy of data measured in the immunological method and can be applied in various fields such as the basic research, medical treatment, drug discovery, inspection and diagnosis.

The present invention solves the problems with the immunological method and the mass spectrometry by mutually complementing the problems and can provide highly-accurate, highly-reliable clinical inspection results.

When the components to be measured are quantified by the immunological method, the differences from the true values, which are caused by the cross-reactivity, are corrected by calculating relative ratios of the components quantified by the mass spectrometry. The quantified values of the components causing the cross-reactivity and the quantified values of the components to be measured are separately calculated by calculating the quantified values of the components.

In addition, an accurate medicinal effect including a metabolite can be calculated on the basis of relative values (related to the medicinal effect) of the components. By using both quantitative values obtained by the simple and high-speed light detection in the immunological method and the calculation of the relative values of the components based on the mass spectrometry, it is possible to mutually complement disadvantages of the measurement methods, or the cross-reactivity in the immunological method and the performance of the quantification in the mass spectrometry, and to achieve a new, simple and high-accuracy clinical inspection technique.

Description of Reference Numerals

101, 501, 1032 . . . Sample, 102, 502 . . . Immunoanalytical system, 103, 503 . . . Immunological pretreatment device, 104 . . . Immunological photometric detection system, 105, 504 . . . Mass spectrometric pretreatment device, 106, 505 . . . Mass spectrometric detection system, 107, 506 . . . Personal computer for system control and data processing, 1031, 1046, 5031, 5046 . . . Dispensing mechanism, 1033, 5033 . . . Specimen rack, 1034, 5034 . . . Reaction vial, 1035 . . . Reaction table, 1036, 5036 . . . Reagent cartridge for immunological method, 1037, 5037 . . . Vial moving mechanism, 1038, 5038 . . . Reaction vial rack, 1039, 5039 . . . Substitution vial, 1041, 1045, 1048, 5045, 5048 . . . Magnet, 1042 . . . Cell, 1043 . . . Light source, 1044 . . . Photometer, 1047 . . . Reaction vial provided with cell, 1049, 5049 . . . Substitution vial rack, 1061, 5061 . . . Ion source, 1062, 5062 . . . Mass spectrometry unit, 1063, 5063 . . . Vacuum pump

The invention claimed is:

1. An immunoanalytical method comprising the steps of:
capturing an object (101, 501, 1032) to be measured, the object being contained in a sample solution, by using an antibody during a pretreatment process based on the immunoanalytical method;
quantifying the captured object (101, 501, 1032) to be measured;
collecting the object (101, 501, 1032) to be measured from a waste liquid resulting after the captured object to be measured has been subjected to the quantification; and
performing mass spectrometry on the collected object to be measured in conformity with a mass spectrometry method and measuring components of the object measured based on the immunoanalytical method.

2. The immunoanalytical method according to claim 1,
wherein, during a pretreatment process based on the immunoanalytical method, the object that is to be measured and is contained in the sample solution is captured by using a primary antibody (204), a secondary antibody (206), and a magnetic particle (201), and the captured object to be measured is irradiated with light for quantification.

3. The immunoanalytical method according to claim 2,
Wherein, the quantified object to be measured is collected by using the primary antibody (204), the secondary antibody (206), and the magnetic particle (201).

4. The immunoanalytical method according to claim 2,
wherein proportions of the components of the object measured based on the immunoanalytical method are calculated by the mass spectrometry method, and a quantitative value for each of the components is corrected by multiplying the quantitative value calculated by the immunoanalytical method by the proportion of the component.

5. The immunoanalytical method according to claim 1,
further comprising the steps of:
capturing an antigen by an antigen-antibody reaction from a waste liquid resulting after the captured object to be measured has been subjected to the quantification; and
collecting the captured antigen after the antigen is liberated,
wherein the mass spectrometry is performed on the collected object to be measured based on the mass spectrometry method.

* * * * *